United States Patent
Lin

(10) Patent No.: US 7,478,910 B1
(45) Date of Patent: Jan. 20, 2009

(54) LIQUID DIAGNOSTIC CONTACT LENS

(76) Inventor: Po-Kang Lin, 5F, No. 201-192, Dorm. Ron-Tzon E. Building, Sec. 2, Shih-Pai, Taipei (TW)

( * ) Notice: Subject to any disclaimer, the term of this patent is extended or adjusted under 35 U.S.C. 154(b) by 0 days.

(21) Appl. No.: 11/960,704

(22) Filed: Dec. 20, 2007

(51) Int. Cl.
*A61B 3/00* (2006.01)
(52) U.S. Cl. ...................................... 351/219
(58) Field of Classification Search ............... 351/200, 351/205, 219
See application file for complete search history.

(56) References Cited

U.S. PATENT DOCUMENTS 5,032,020 A * 7/1991 Robert ....................... 351/219

* cited by examiner

*Primary Examiner*—Huy K Mai

(57) ABSTRACT

A liquid diagnostic contact lens includes a main body having a concave lens, and a supporting element disposed at a bottom of the main body. A heavy fluid is placed on a top surface of the concave lens. A transparent plate is sealed over the top surface of the concave lens so as to define an encapsulating room and encapsulate the heavy fluid therein. In operation, an ophthalmologist places the supporting element onto the eye, and examines various interior spots of the eye by adaptively adjusting the eye. The liquid diagnostic contact lens is tilted along with the eye and the top surface of the heavy fluid is kept horizontal so the heavy fluid is formed as prisms of different diopters. Thus, the liquid diagnostic contact lens can examine various spots of the interior of the eye.

6 Claims, 5 Drawing Sheets

LIQUID DIAGNOSTIC CONTACT LENS

BACKGROUND OF THE INVENTION

1. Field of the Invention

The present invention relates generally to a magnification device for ophthalmic examination and surgery.

2. The Prior Arts

When conducting a diagnostic examination or a therapeutic procedure to an eye, an ophthalmologist often needs to use opthalmoscope, diagnostic contact lens, slit lamp, or ultrasound device, etc. to diagnose the eye condition and then treat thereby.

A conventional diagnostic contact lens is a flat lens, a concave lens, or a prism. A flat lens is often used for examining a posterior pole of the eye. However, in viewing a peripheral retina, various prisms of different diopters are often required. The ophthalmologist directly places the prism onto the eye. The prism is turned or replaced with another one having a different diopter according to the position to be examined. It is inconvenient to use and may even accidentally cause eye injuries.

SUMMARY OF THE INVENTION

A primary objective of the present invention is to provide a liquid diagnostic contact lens for ophthalmic diagnostic examination or a therapeutic procedure. The liquid diagnostic contact lens can be directly placed on a surface of an eye. Moreover, the liquid diagnostic contact lens can be adjusted to view a wide range of the eye, such as from the posterior pole to the peripheral retina, without turning or replacing with another liquid diagnostic contact lens. The operation of the liquid diagnostic contact lens not only saves a lot of time, but also drastically eliminates the risk of accidental injury to the eye.

The liquid diagnostic contact lens is a magnifying lens specifically adapted for ophthalmic inspections or operations. According to an embodiment of the present invention, the liquid diagnostic contact lens includes a main body having a concave lens configured thereto, and a supporting element configured at a lower portion of the main body. The concave lens has a top surface, on which a heavy fluid is adaptively placed. A transparent plate is employed over the top surface of the concave lens so as to define an encapsulating room and encapsulate the heavy fluid therein. In operation, an ophthalmologist may place the supporting element onto the eye, and views various interior spots of the eye by adaptively adjusting the eye. The liquid diagnostic contact lens is tilted along with the eye. The top surface of the heavy fluid is kept in a horizontal level due to gravity so the heavy fluid is formed as a flat lens or a prism having adjustable diopters.

According to the present invention, the main body itself can be a concave lens, or otherwise includes a concave lens equipped thereto.

According to another embodiment of the present invention, in addition to the heavy fluid, the encapsulating room may further have at least another fluid with specific gravity different from the heavy fluid, such as oil, received therein, so as to modify the optical refraction characteristics of the liquid diagnostic contact lens.

According to still another embodiment of the present invention, the supporting element can be either integrally formed with the main body, or individually formed and later equipped at a lower portion of the main body. In the case that the supporting element is individually formed, the supporting element has an annular wall, whose bottom includes a cone shaped supporting base extended therefrom. The lower portion of the main body is fitted into the annular wall of the supporting element.

The liquid diagnostic contact lens according to the present invention is kept on a fixed position of the eye without turning or replacing diagnostic contact lens, and can examine the eye simply by adjusting the position and angle of the eye. In such a way, the operation is simple, convenient, and will not injure the eye.

BRIEF DESCRIPTION OF THE DRAWINGS

The present invention will be apparent to those skilled in the art by reading the following detailed description of preferred embodiments thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
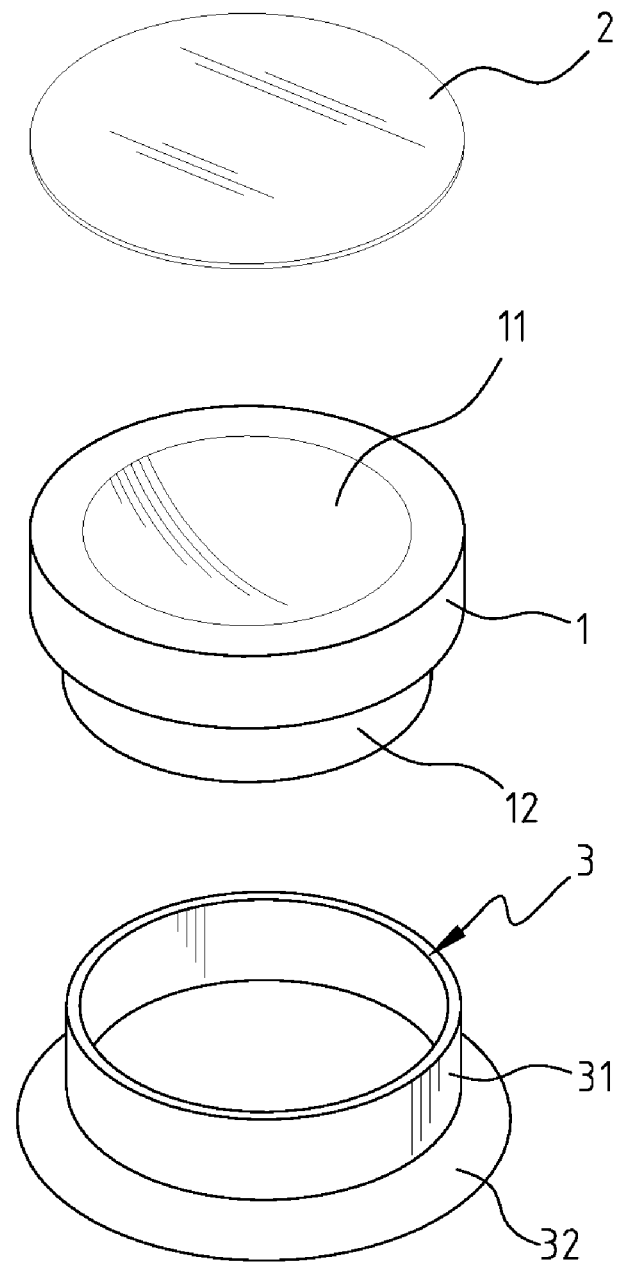
FIG. 1 is an exploded view showing a liquid diagnostic contact lens according to an embodiment of the present invention.
Figure 2:
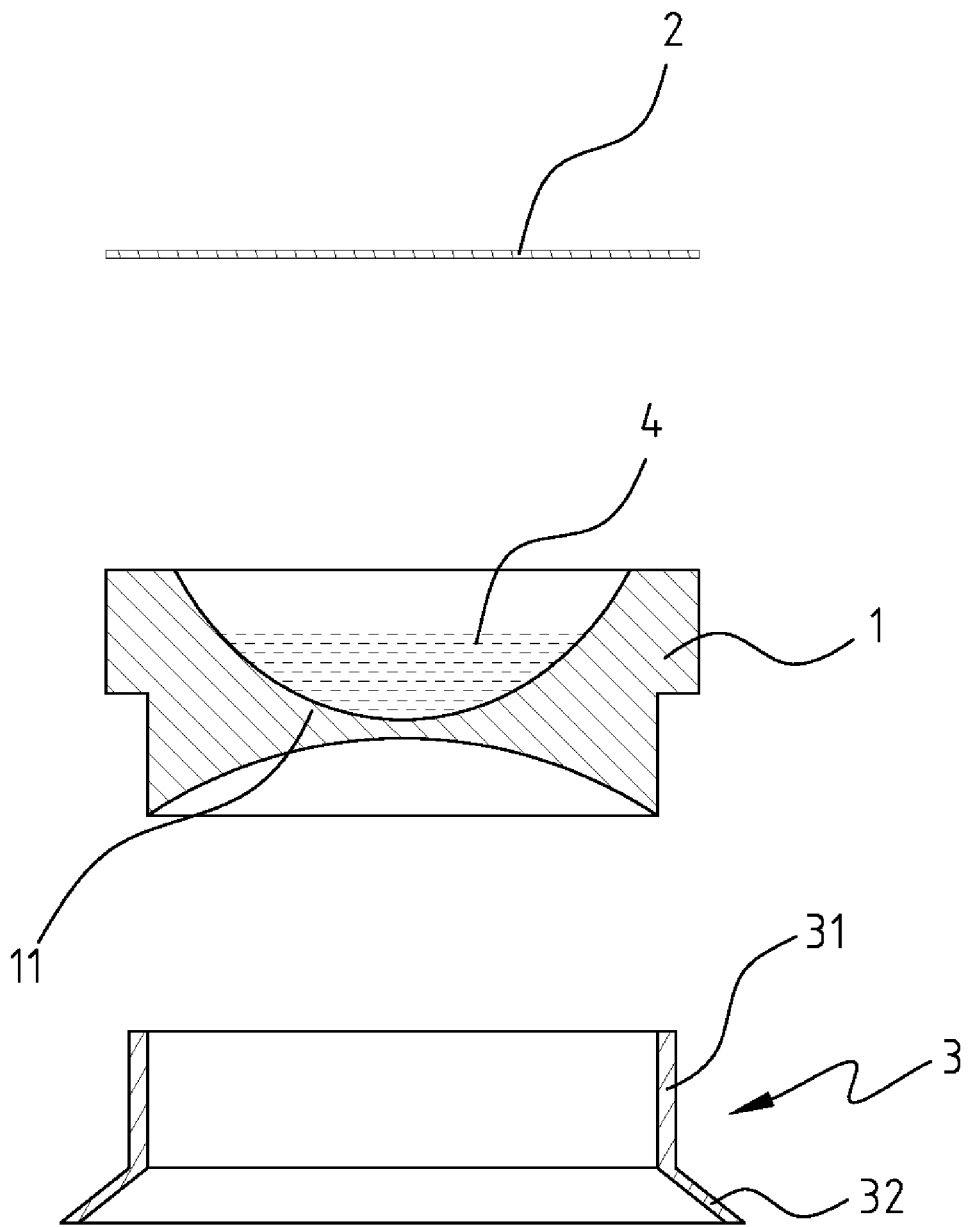
FIG. 2 is an exploded cross-sectional view illustrating the liquid diagnostic contact lens shown in FIG. 1.
Figure 3:
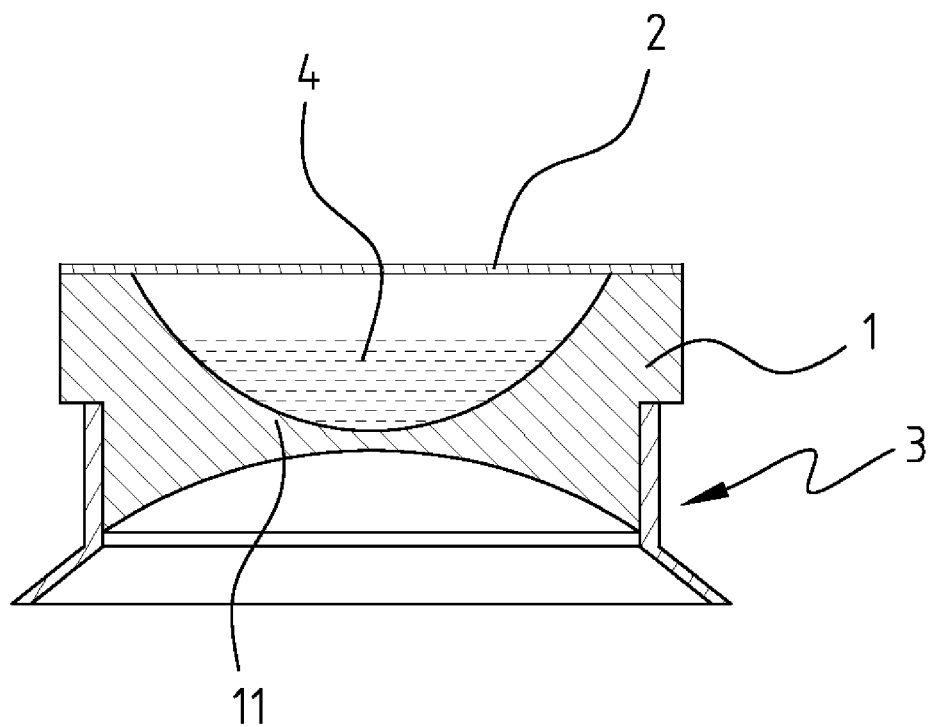
FIG. 3 is a cross-sectional view showing the liquid diagnostic contact lens of FIG. 2 after being assembled.

FIGS. 1 to 3 illustrate a liquid diagnostic contact lens adapted for ophthalmic inspections or operations according to a first embodiment of the present invention. The liquid diagnostic contact lens includes a main body 1, a transparent plate 2, a supporting element 3, and a suitable heavy fluid 4. The main body 1 includes a concave lens 11 configured integrally at a center thereof, and a lower portion 12 configured integrally at a bottom thereof. The lower portion 12 is adapted for engaging with the supporting element 3. The concave lens 11 has a top surface and a bottom surface. The top surface of the concave lens 11 is a concave surface having a certain curvature which is not restricted by the present invention. A space is defined between the top surface of the concave lens 11 and an upper surface of the main body 1. The heavy fluid 4 is received in the space, and encapsulated by the transparent plated 2 disposed on the upper surface of the main body 1. The transparent plate 2 can be fixed onto the upper surface of the main body 1 by high frequency sealing, or be adhered to the upper surface of the main body 1 with adhesive. Therefore, the space between the top surface of the concave lens 11 and the transparent plate 2 is formed as an airtight encapsulating room which encapsulates the heavy fluid 4 therein. Instead of the integrally-formed concave lens 11 and main body 1, the concave lens 11 and the cylindrical main body 1 may be two separated pieces (not shown in Figures). The concave lens 11 is tightly fitted into the inside of the main body 1.

The heavy fluid 4 is a fluid having a specific gravity greater than that of water. The heavy fluid 4 is a medium for cooperating with the concave lens 11 to determine the optical refraction characteristics. As such, according to another embodiment of the present invention, at least another fluid having a specific gravity different from the heavy fluid 4 is further introduced into the encapsulating room. In such a way, the encapsulating room has a mixture of the heavy fluid 4 and at least another fluid received therein. For example, the another fluid can be oil, which has a smaller specific gravity than the heavy fluid 4. When received in the encapsulating room, the heavy fluid 4 stays under the another fluid, because of its greater specific gravity. For example, when the encapsulating room has a mixture of the heavy fluid 4 and three another fluids received therein, there are four layers of fluids received in the encapsulating room.

The supporting element 3 is made of a hypoallergenic material, such as silicone or the like. The supporting element 3 includes an annular wall 31, and a cone shaped supporting base 32 extended from a bottom of the annular wall 31. The lower portion 12 of the main body 1 is fitted into an inside of the annular wall 31 of the supporting element 3. The supporting base 32 configures a part of a cone whose diameter enlarges as the supporting base 32 extends, thereby preventing the supporting base 32 from blocking the view in operation.

The bottom surface of the concave lens 11 is also a concave surface. The curvature of the bottom surface of the concave lens 11 is designed to adapt to a general shape of a human eye.

Figure 4:
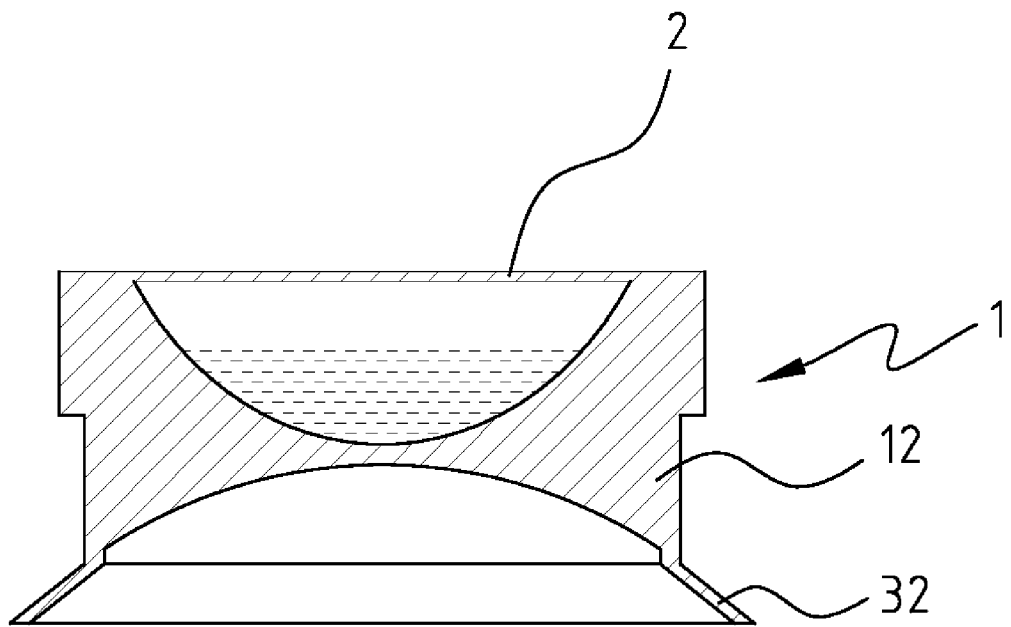
FIG. 4 is a cross-sectional view illustrating a liquid diagnostic contact lens according to another embodiment of the present invention.

Referring to FIG. 4, the supporting base 32 according to still another embodiment of the present invention is made of silicone or other materials which won't cause allergic reaction to human body, and is integrally formed with the main body 1.

Figure 5:
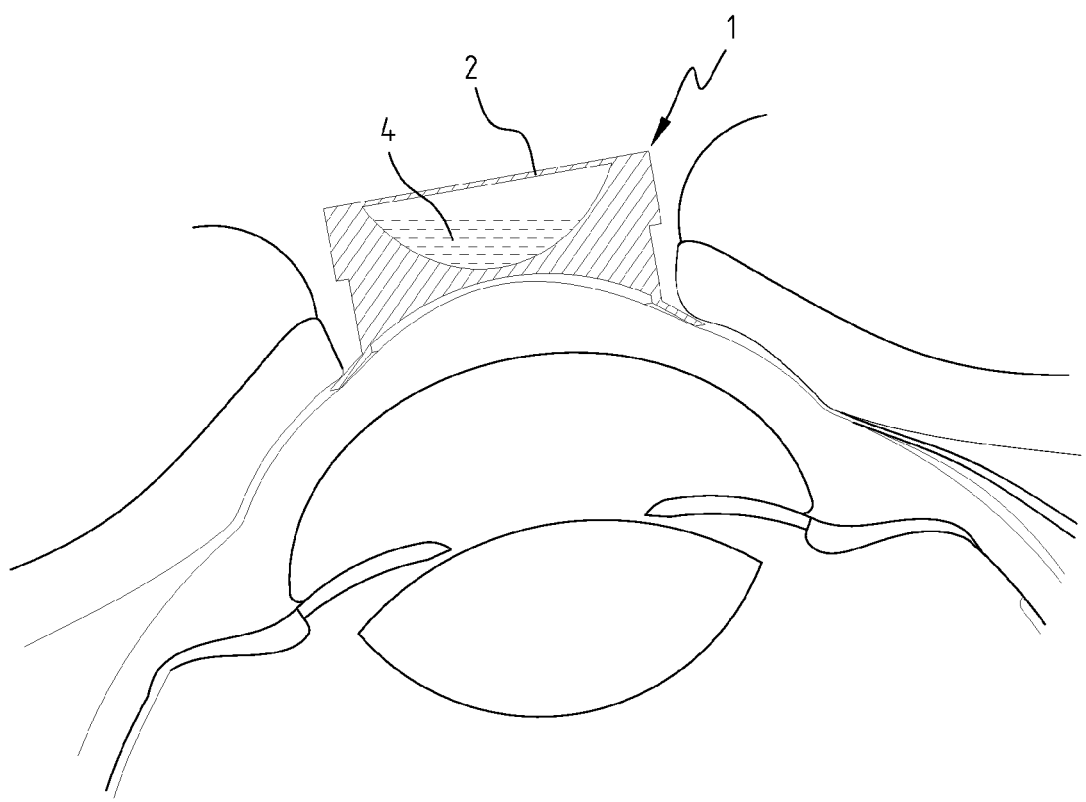
FIG. 5 is a schematic view illustrating a practical operation of the liquid diagnostic contact lens according to the present invention.

FIG. 5 is a schematic view illustrating the liquid diagnostic contact lens according to the present invention on an examined eye. In practical operation, an ophthalmologist places the liquid diagnostic contact lens directly onto the eye, and adaptively adjusts a position or an angle of the eye. Associating with the adjustment of the eye, the main body 1 is correspondingly tilted. Even though the main body 1 is tilted in accordance with the adjustment made to the eye, a top surface of the heavy fluid 4 is maintained horizontal due to the gravity. As such, corresponding to different position of the concave lens 11, the heavy fluid 4 is featured with different thickness, so as to configure a liquid prism. In facilitation with such a liquid prism and the concave lens 11, the ophthalmologist can get a better view to the interior of the eye. The operation of the liquid diagnostic contact lens on the eye can be achieved simply by adjusting the position and the angle of the eye and does not need to turn or replace the diagnostic contact lens. In such a way, the operation is simple, convenient, and won't injure the eye.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A liquid diagnostic contact lens, comprising:
a main body having a concave lens;
a heavy fluid disposed on a top surface of the concave lens;
a transparent plate airtightly attached to an upper surface of the main body, and forming an airtight encapsulating room between the top surface of the concave lens and the upper surface of the main body; and
a supporting element disposed at a bottom of the main body;
wherein the heavy fluid is received in the encapsulating room.

2. The liquid diagnostic contact lens according to claim 1, wherein the concave lens is integrally formed with the main body.

3. The liquid diagnostic contact lens according to claim 1, wherein the encapsulating room further comprises at least another fluid having a specific gravity different from the heavy fluid received therein and mixed with the heavy fluid.

4. The liquid diagnostic contact lens according to claim 3, wherein the another fluid is oil.

5. The liquid diagnostic contact lens according to claim 1, wherein the supporting element comprises an annular wall and a cone shaped supporting base extended from a bottom of the annular wall, and a lower portion of the main body is tightly fitted into an inside of the annular wall.

6. The liquid diagnostic contact lens according to claim 1, wherein the supporting element is cone shaped, integrally formed with the main body and directly extended from a lower portion of the main body.

* * * * *